(12) United States Patent
Asami et al.

(10) Patent No.: US 8,926,948 B2
(45) Date of Patent: Jan. 6, 2015

US008926948B2

(54) PROCESS AND APPARATUS FOR PREPARING A DIAGNOSTIC OR THERAPEUTIC AGENT

(75) Inventors: Rei Asami, Kawasaki (JP); Kenichi Kawabata, Kodaira (JP)

(73) Assignee: Hitachi, Ltd., Tokyo (JP)

( * ) Notice: Subject to any disclaimer, the term of this patent is extended or adjusted under 35 U.S.C. 154(b) by 1534 days.

(21) Appl. No.: 12/163,244

(22) Filed: Jun. 27, 2008

(65) Prior Publication Data

US 2009/0010852 A1    Jan. 8, 2009

(30) Foreign Application Priority Data

Jul. 2, 2007    (JP) .................................. 2007-174239

(51) Int. Cl.
- *A61B 8/00* (2006.01)
- *A61K 47/48* (2006.01)
- *A61K 49/22* (2006.01)

(52) U.S. Cl.
CPC .............. *A61K 47/488* (2013.01); *A61K 49/223* (2013.01)
USPC ........................................................ 424/9.5

(58) Field of Classification Search
None
See application file for complete search history.

(56) References Cited

U.S. PATENT DOCUMENTS 5,716,597 A * 2/1998 Lohrmann et al. ............ 600/458
2008/0311046 A1  12/2008 Kawabata et al.

FOREIGN PATENT DOCUMENTS

WO    01/08464 A2    2/2001

OTHER PUBLICATIONS

Kawabata K, Yoshizawa A, Asami R, Azuma T, Yoshikawa H, Watanabe H, Sasaki K, Hirata K, Umemura S. Site-specific contrast imaging with locally induced microbubbles from liquid precursors. 2006 IEEE Ultrasonics Symposium Oct. 2-6: 517-520.*
Pisani E, Tsapis N, Paris J, Nicolas V, Cattel L, Fattal E. Polymeric nano/microcapsules of liquid perfluorocarbons for ultrasonic imaging: physical characterization. 2006 Langmuir 22: 4397-4402.*
K. Kawabata et al., Jpn. Journal of Applied Physics, vol. 44, pp. 4548-4552 Jun. 24, 2005.
S. Shinoda et al., Journal of Colloid and Interface Science 26, pp. 70-74, 1968.
O. Kripfgans et al., Ultrasound in Med. & Biol., vol. 26, No. 7, pp. 1177-1189, 2000.
S. Umemura et al., Proc. IEEE Ultrasonics Symposium 2, pp. 1311-1314, 2001.

* cited by examiner

*Primary Examiner* — Michael G Hartley
*Assistant Examiner* — Jennifer Lamberski
(74) *Attorney, Agent, or Firm* — Mattingly & Malur, PC

(57) ABSTRACT

Provided are a preparation process of a diagnostic or therapeutic agent having a step of adding, to a first fine emulsion having a particle size of 0.5 μm or less prepared by applying a predetermined pressure to a first mixture containing a first hydrophobic compound, an emulsifying agent, and an aqueous phase, a second hydrophobic compound compatible with the first hydrophobic compound, thereby preparing a second mixture; and a step of stirring and shaking the second mixture in a hermetically sealed state, thereby embedding the second hydrophobic compound in the first fine emulsion to prepare a second fine emulsion having a particle size of 0.5 μm or less; a diagnostic or therapeutic agent prepared by the process; and an apparatus for carrying out the process.

13 Claims, 3 Drawing Sheets

PROCESS AND APPARATUS FOR PREPARING A DIAGNOSTIC OR THERAPEUTIC AGENT

CLAIM OF PRIORITY

The present application claims priority from Japanese patent application JP 2007-174239 filed on Jul. 2, 2007, the content of which is hereby incorporated by reference into this application.

CROSS-REFERENCE TO RELATED APPLICATION

This application is related to U.S. patent application Ser. No. 11/778,255 filed on Jul. 16, 2007, the disclosure of which is hereby incorporated by reference.

FIELD OF THE INVENTION

The present invention relates to an apparatus and process for preparing a diagnostic or therapeutic agent.

An ultrasonic diagnostic apparatus is an apparatus for visualizing a difference in an acoustic impedance of a material in a body, that is, a physical property defined as density multiplied by an acoustic velocity. It is an image diagnostic modality which has a relatively small and inexpensive structure compared with X-ray CT or MRI and is usable even for prenatal testing because it does not require exposure to radiation or magnetism and is therefore minimally invasive. Conventionally, it has been used particularly for medical examination. Due to recent improvement in image quality and function, the ultrasonic diagnostic apparatus is used not only for medical examination but also for precise diagnosis. In particular, detailed imaging of a pathologic condition while using a contrast agent has drawn increasing attention.

The most popular ultrasonic contrast agent at present is a micron-size bubble (microbubble) agent stabilized by a surfactant or the like. This microbubble contrast agent is suited for the visualization of blood vessels but an agent of a different form is necessary for the visualization of tissues other than blood vessels. A phase shift contrast agent is suited for such a purpose from the standpoints of delivery to tissues and sensitivity (K. Kawabata et al., *Jpn. J. Appl. Phys.* 44, 4548 (2005)). The phase shift contrast agent produces bubbles by encapsulating a hydrophobic liquid having a low boiling point under a superheated state in advance and evaporating the liquid at a target site by breaking the superheated state by ultrasonic pulses to restore the boiling point of the liquid to its original one. The agent has a particle size adjusted to be 0.5 µm or less enables realization of delivery of the agent to tissues other than the blood vessels, which cannot be realized easily by microbubbles. The agent is especially suited as an ultrasonic contrast agent for detailed visualization of diseased tissues.

The phase shift contrast agent can be used not only for diagnosis by evaporating it at a target tissue but also for the purpose of treatment. In particular, it is useful as a sensitizer for thermal coagulation therapy using HIFU (High Intensity Focused Ultrasound). When ultrasonic waves are irradiated in the presence of microbubbles, an apparent ultrasonic absorption coefficient of the system increases and an energy absorbed is converted into heat so that a local temperature rise occurs in the vicinity of bubbles (S. Umemura et al., *Proc. IEEE Ultrasonics Symposium* 2, 1311(2001)). Use of this phenomenon enables site-selective thermal coagulation therapy with ultrasonic waves.

The phase shift contrast agent is morphologically a submicron-size fine emulsion and it is prepared typically by mixing a surfactant with a hydrophobic liquid having a low boiling point in a normal-pressure emulsifier and reducing the particle size of the resulting mixture to 1 µm or less by high-pressure emulsification. An emulsifier employed for high-pressure emulsification is usually large and has therefore low portability. The PIT method (S. Shinoda et al., *J. Colloid Interface Sci.*, 26, 70(1968)) is one example of a method for obtaining a phase shift contrast agent by using only an emulsifier having high portability, but it is not used generally because a surfactant or inclusion usable is limited in this method. Although there is a report on "a relatively simple preparation process of an emulsion with a desktop type agitator" (O. Krifptgan et al., *Ultrasound in Med. & Biol.*, 26, 1177(2000)), the process cannot easily prepare particles having a size of 1 µm or less.

SUMMARY OF THE INVENTION

The above-described phase shift contrast agent needs deliberate care in temperature control during storage or transportation because it contains a hydrophobic compound having a low boiling point. A change in the concentration or proportion of components may occur between just after preparation and after storage, depending on the storage condition. Limitation in use is therefore a conventional problem particularly when a plurality of hydrophobic compounds are mixed and in vivo residence or sensitivity to external stimuli such as ultrasonic waves must be controlled. In order to use an agent containing these hydrophobic compounds at a precisely controlled mixing ratio, it is effective not to prepare the agent in advance by mixing them but to prepare the agent just before use. The conventional preparation process however is not suited for preparation of the agent just before use, because it requires a large-sized apparatus such as high-pressure emulsifier. As described above, it is known to prepare the agent just before use by using not a large-sized apparatus such as high-pressure emulsifier but an amalgamator. The contrast agent prepared by this process has, however, a particle size of several microns or greater and therefore is not suited for use in tissues other than blood vessels.

An object of the present invention is therefore to provide a process for preparing a contrast agent having a particle size not greater than a micron size by using a simple apparatus, which process was difficult to achieve by the related art.

With a view to achieving the object, the present inventors have carried out an intensive investigation on a process facilitating preparation of components included in a fine emulsion just before use, particularly a process capable of preparing an O/W fine emulsion, typified by a phase shift contrast agent, including therein a plurality of hydrophobic substances at a desired concentration ratio without impairing the portability of an emulsifier to be employed.

As a result, it has been found that by mixing a second hydrophobic compound in a first fine emulsion prepared by including therein a first hydrophobic compound and stirring the resulting mixture, a second fine emulsion embedding therein desired amounts of the first and second hydrophobic compounds and having a particle size of 0.5 µm or less can be prepared, leading to the completion of the present invention.

In one aspect of the present invention, there is thus provided a process of preparing a diagnostic or therapeutic agent, which includes: adding a second hydrophobic compound to a first fine emulsion having a diameter of 0.5 µm or less which is prepared by applying a pressure to a first mixture comprising a first hydrophobic compound, an emulsifying agent, and an aqueous phase, thereby preparing a second mixture; and stirring the second mixture in a hermetically sealed state to embed the second hydrophobic compound in the first fine emulsion, thereby obtaining a second fine emulsion having a diameter of 0.5 µm or less. This process enables determination of a proportion of a high-boiling-point compound and a low-boiling-point compound present in the fine emulsion of a phase shift contrast agent just before use and control of the properties of the phase shift contrast agent such as in vivo residence time and ultrasonic sensitivity as needed.

Although no particular limitation is imposed on the first and second hydrophobic compounds insofar as their biotoxicity is low, they contain preferably at least one compound selected from linear hydrocarbons, branched hydrocarbons, linear fluorinated hydrocarbons, and branched fluorinated hydrocarbons.

In combined use of the first hydrophobic compound and second hydrophobic compound, compatibility and intensity of their mutual action are important. They are required to have a chemical structure as similar as possible. A preferred relationship between them is that one of the compounds has a structure obtained by adding a hydrophobic functional group such as alkyl group to the other compound or that one of the compounds is a hydrophobic compound having a low boiling point and the other one is preferably an analog thereto obtained by substituting three or fewer fluorine atoms of the compound with hydrogen atoms.

It is preferred that one of the hydrophobic compounds is, as described by Kawabata et al. (in the above-described document), in the liquid form upon administration and has a low boiling point less than 37°, while the other component has a boiling point of 37° or greater. Examples of such a low-boiling point and hydrophobic compound include perfluoro-n-pentane and isopentane, while those of the high-boiling point and hydrophobic compound include perfluorohexane, perfluoroheptane, perfluorooctane and hexane.

No limitation is imposed on the emulsifying agent to be used in the present invention insofar as it is a surfactant having high biocompatibility as described by Kawabata et al. Examples of it include lipid mixtures such as phospholipids and cholesterol, vitamin E derivatives, and proteins soluble in both water and lipid such as albumin. Alternatively, a water-soluble polymer such as polyethylene glycol may be used and in this case, the surface of the fine emulsion may be covered with it.

Although no particular limitation is imposed on the dispersion medium of the fine emulsion particles in the present invention insofar as it has biocompatibility, physiological saline and phosphate buffer are especially preferred.

In the preparation process of an agent according to the present invention, a stirring unit is maintained preferably at the melting point of the aqueous phase employed or greater, more specifically, at 10° C. or less, preferably 0° C. or greater but not greater than 10° C.

The stirring step is performed preferably at a rate of approximately 3000 rpm or greater.

In another aspect of the present invention, there is also provided a diagnostic or therapeutic agent prepared by the above-described process. The diagnostic or therapeutic agent according to the present invention includes a second fine emulsion having a particle size of 0.5 µm or less obtained by embedding at least one compound selected from perfluoro-n-pentane and isopentane in a first fine emulsion having a particle size of 0.5 µm or less and containing at least one compound selected from perfluorohexane, perfluoroheptane, perfluorooctane, and hexane, an emulsifying agent, and an aqueous phase. The agent is usable mainly as a contrast agent.

In a further aspect of the present invention, there is also provided an apparatus for preparing a diagnostic or therapeutic agent while using the process of the present invention. The apparatus is equipped with a storing unit which stores a first liquid, a reservoir unit which reserves a second liquid, a stirring unit which stirs a content stored in the storing unit, a temperature regulating unit which regulates a temperature of at least any of the storing unit, the reservoir unit, the stirring unit, and the stirring unit, and a control unit which controls the storing unit, the reservoir unit, the stirring unit, and the stirring unit.

In the apparatus of the present invention, the stirring unit is preferably designed to permit stirring at a rate of 3,000 rpm or greater in a hermetically sealed state while controlling the temperature to be at 0° C. or greater but not greater than 10° C.

The present invention makes it possible to prepare a phase shift contrast agent just before use while controlling the properties of it such as in vivo residence time and ultrasonic sensitivity. The process of the present invention is suited as a preparation process just before use because it is excellent in portability of an emulsifier to be employed and needs only a short time for preparation. In addition, the agent can be provided in a highly antiseptic and stabilized condition without exposing it throughout the steps.

DETAILED DESCRIPTION OF THE PREFERRED EMBODIMENTS

The present invention will hereinafter be described by examples in detail. It should however be borne in mind that the present invention is not limited to these examples.

First Example

Preparation Process of an Agent Just Before Use

First, 0.1 g of soybean-derived phosphatidyl choline and 0.05 g of cholesterol were dissolved in chloroform. The resulting solution was poured in a water tank of 37° C. and dried under reduced pressure. To the residue was added 20 mL of a phosphate buffered saline and 1 second pulse was applied to the resulting mixture for 5 minutes by using an ultrasonic homogenizer to yield a liposome. To the resulting solution was added from 1 to 5% (v/v) of perfluorohexane and the resulting mixture was homogenized at 9,500 rpm at an ice temperature for one minute. The emulsion thus obtained was subjected to high-pressure emulsification treatment at 20 MPa for 5 minutes in "Emulsiflex-C5" (trade name; product of Avestin, Ottawa/Canada), followed by filtration through a membrane filter having a pore size of 0.45 μm. The above-described treatment yielded an almost clear emulsion. As a result of measurement using a particle size analyzer ("LB-550", trade name; product of Horiba, Ltd./Tokyo), the emulsion thus obtained was determined to have an average particle size of approximately 100 nm. By the above-described steps, a stock emulsion was obtained. The stock emulsion was stable for 6 months or more in a refrigerator (4° C.).

Figure 1:
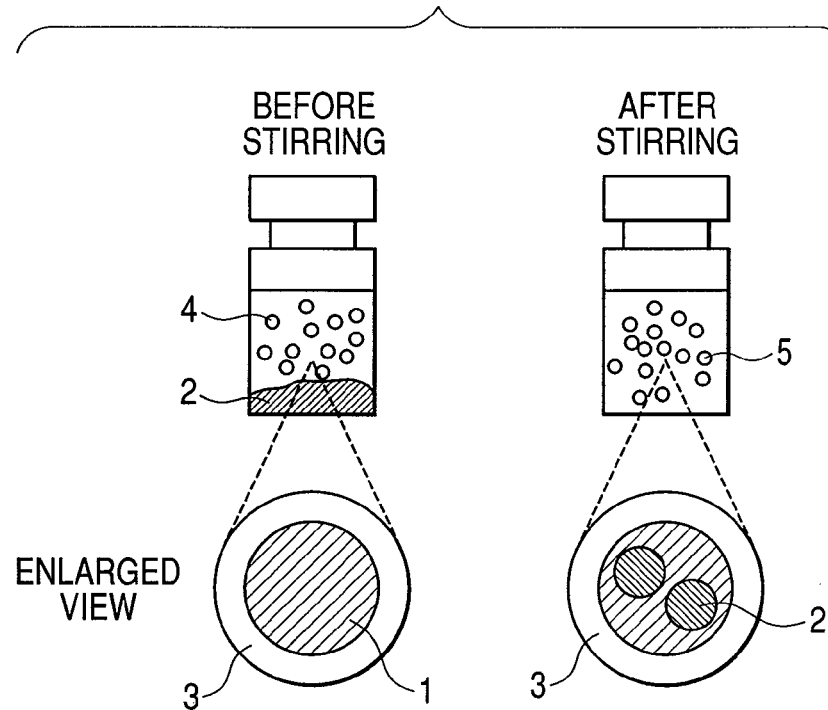
FIG. 1 is a schematic view illustrating the partial concept of the preparation process of a contrast agent according to the present invention.

Preparation of a phase shift contrast agent just before use, which was performed following the preparation of the stock emulsion, will next be described referring to FIG. 1. After the above-described stock emulsion, which was a first fine emulsion 4 containing perfluorohexane as a first hydrophobic compound 1 and an emulsifying agent 3, was filled in a 2-mL vial and hermetically sealed with a rubber cap. From 1 to 5% perfluoro-n-pentane was added as a second hydrophobic compound 2 via an injection syringe while cooling the vial on ice. The resulting mixture was stirred for 5 seconds at a rate of 3,000 rpm in the vial maintained at 4° C. to yield a crude second fine emulsion 5. The stirring time for 5 seconds is a time until the emulsion and perfluoro-n-pentane added subsequently form an apparently single phase without causing a phase separation and it can be controlled, depending on the kind, total amount or proportion of the solution to be added. Although a higher stirring rate produces a higher stirring effect, it raises the temperature of the sample simultaneously, making it impossible to obtain a fine emulsion having a target particle or globule size. In this example, a similar effect to that brought by stirring at 3000 rpm is available when stirred at a rate of 4000 or 6000 rpm.

Figure 2:
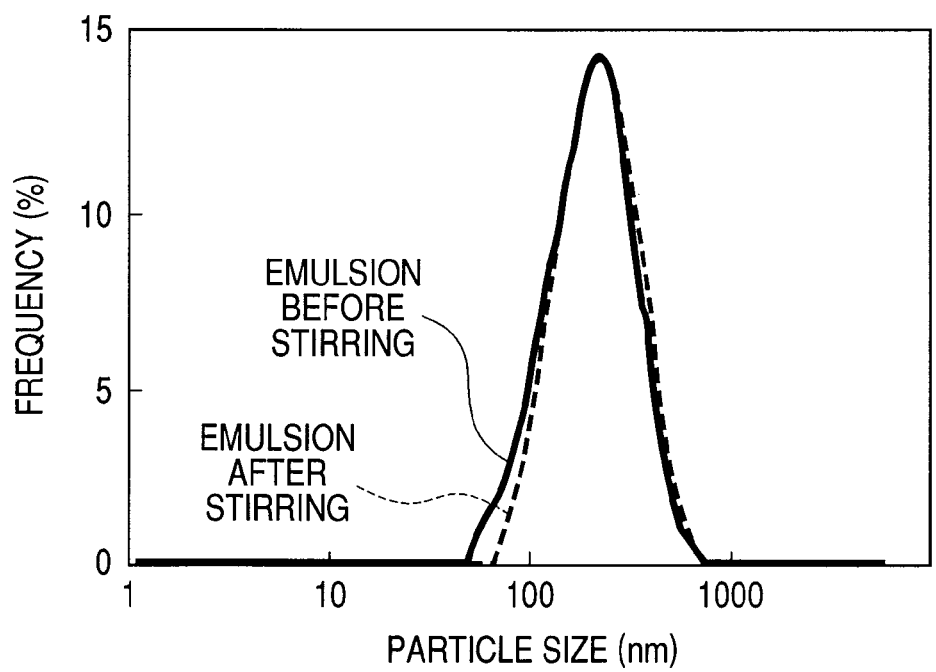
FIG. 2 illustrates one example of the analysis results of the particle size distribution of the emulsion prepared in accordance with the present invention.
Figure 3:
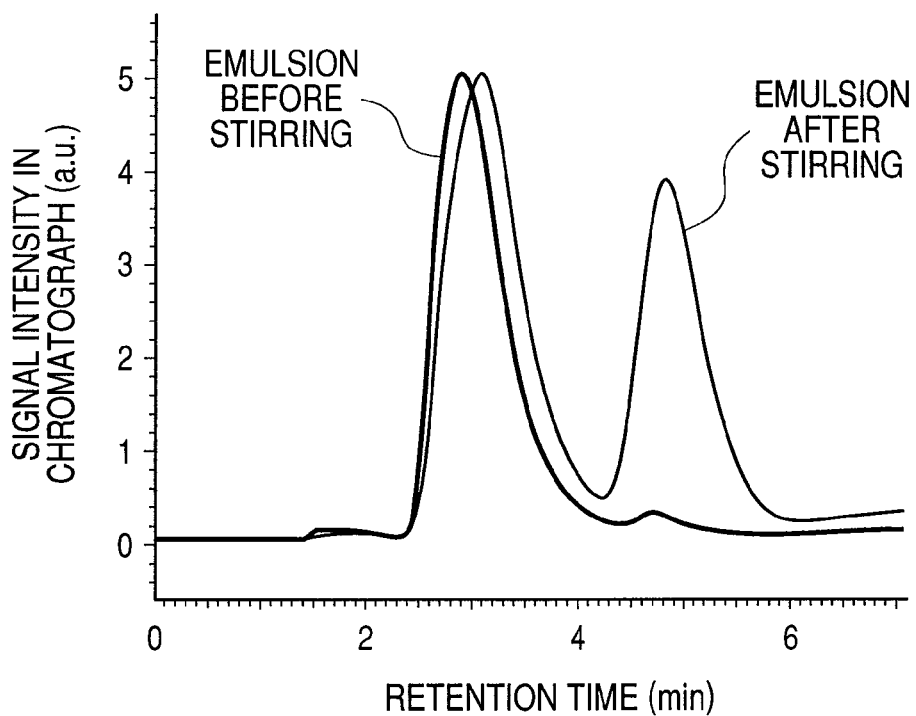
FIG. 3 illustrates one example of the analysis results of components included in the emulsion prepared in accordance with the present invention.

In order to remove foreign matters such as bubbles generated by stirring, the crude second fine emulsion 5 was filtered through a membrane having a pore size of 0.45 μm. As a result, the second fine emulsion 5 containing the first hydrophobic compound 1 and the second hydrophobic compound 2 in the emulsifying agent 3 was obtained. Measurement results of the particle size distribution of the emulsion thus obtained by using the above-described particle size analyzer are shown in FIG. 2. FIG. 2 has revealed that the emulsion before stirring and the emulsion after stirring are much the same in particle size distribution and an average particle size is 0.5 μm or less. An inclusion of the emulsion obtained after stirring was analyzed using a gas chromatograph analyzer "G-6000" (trade name; product of Hitachi High-Technologies/Tokyo) and the results are shown in FIG. 3. It has been confirmed that only a peak of perfluorohexane is observed from the emulsion before stirring, while perfluoro-n-pentane included therein is observed from the emulsion after stirring as a result of stirring. These findings suggest that the process of the present invention is effective for embedding perfluoro-n-pentane in perfluorohexane while keeping the particle size at 0.5 μm or less.

Test 1: Control Effect of In-Vivo Residence Time of the Agent

The result of a study on the control effect of the in-vivo residence time of the fine emulsion prepared in the first example will be described. The present fine emulsion contains a hydrophobic compound (perfluoro-n-pentane) having a low boiling point so that its stability highly depends on temperatures. Evaluation was performed while using, as an index, a content of perfluoro-n-pentane, that is, an effective ingredient in a liquid phase in a temperature-controlled bath which simulated the internal body temperature of 37° C.

Figure 4:
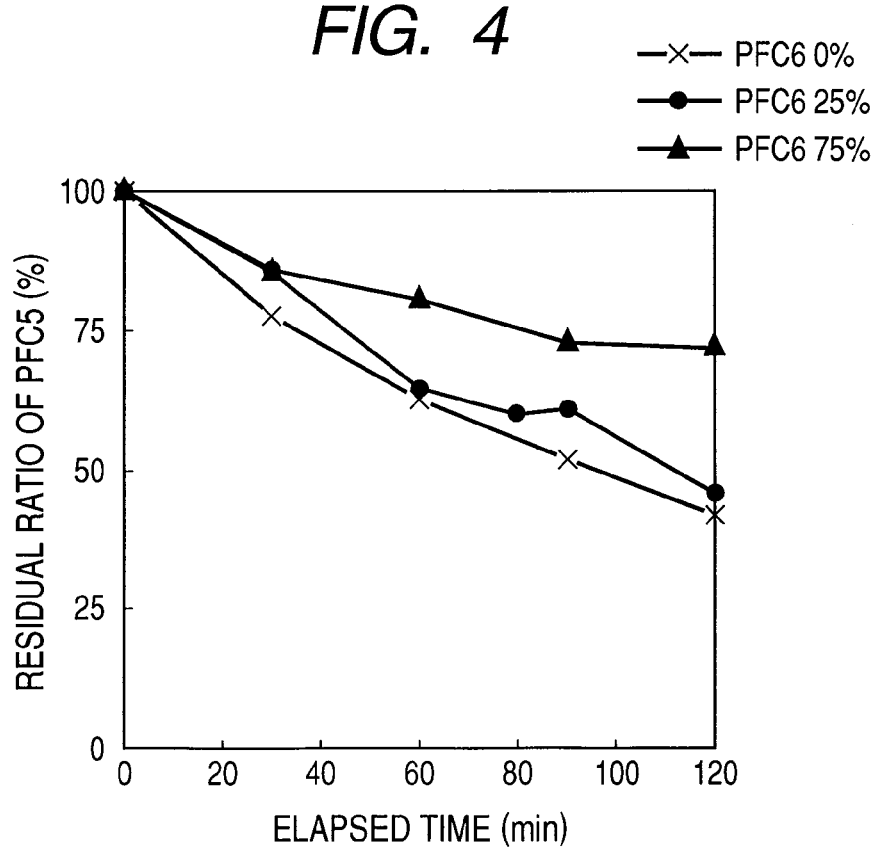
FIG. 4 illustrates one example of a test showing the effect of the emulsion prepared in accordance with the present invention on the in-vivo residence time.

The fine emulsion diluted with physiological saline was poured into an open-type vessel. The vessel was fixed in the temperature-controlled bath set at 37° C. and a content of perfluoro-n-pentane from the liquid phase was determined with the passage of time. One example of the results is shown in FIG. 4. An increase in the proportion of perfluorohexane relative to perfluoro-n-pentane present in the fine emulsion was effective for raising a residual ratio of perfluoro-n-pentane. This suggests that the in vivo residence time can be controlled by changing the proportion of perfluorohexane to be included. Similar effect was available by the use of perfluoroheptane or perfluorooctane instead of perfluorohexane.

Second Example

Process of Preparing a Fine Emulsion Containing Water Soluble Polymer Just Before Use (Modification of the First Example)

In a similar manner to the first example except that in addition to 0.1 g of soybean-derived phosphatidyl choline and 0.05 g of cholesterol, 0.05 g of phosphatidyl ethanolamine added with polyethylene glycol (having a molecular weight of 2000) was used as the emulsifying agent, a fine emulsion was obtained. The resulting emulsion had the same properties as those of the fine emulsions of the first example and Test 1.

Third Example

Process of Preparing a Fine Emulsion Containing a Mixture of Isopentane with Hexane (Modification of the First Example)

In a similar manner to the first example except that perfluorohexane and perfluoro-n-pentane were replaced by hexane and isopentane, respectively, a fine emulsion was prepared. The emulsion thus obtained had the same properties as those of the fine emulsion of the first example and Test 1.

Fourth Example

Process of Preparing a Fine Emulsion Containing Albumin (Modification of the First Example)

In a similar manner to the first example except that 3 g of albumin was used as the emulsifying agent, a fine emulsion was prepared. The emulsion thus obtained had the same properties as those of the fine emulsion of the first example and Test 1.

Fifth Example

Apparatus for Preparing an Agent Just Before Use

An example of a preparation apparatus to be used in the present invention will next be described specifically referring to a structure diagram shown in FIG. 5. The diagram is a partially schematic view and does not illustrate a concrete design of the apparatus.

Figure 5:
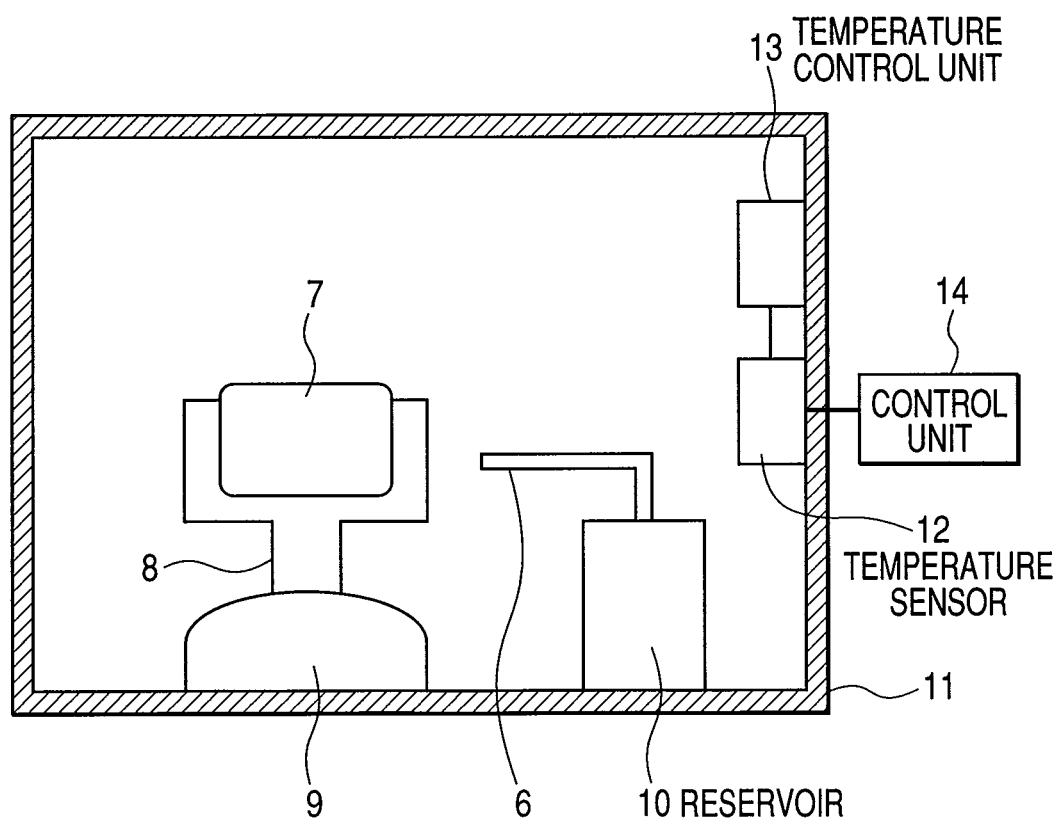
FIG. 5 illustrates the structure of one example for the preparation of a contrast agent in accordance with the method employed in the present invention.

As illustrated in FIG. 5, the present apparatus is equipped with a reservoir unit 10 for storing therein the second hydrophobic compound, a fixing unit 8 of a vessel 7 containing the first mixture, a high-speed stirring unit 9 connected to the fixing unit, and a feed pipe 6 for adding a predetermined amount of the second hydrophobic compound to the vessel 7 containing the first fine emulsion. All the above-described units are arranged in a hermetic seal type box 11. Further, the apparatus is equipped with a temperature sensor 12 and a temperature control unit 13 (providing heating/cooling) connected thereto for regulating temperatures, and an external control unit 14.

The vessel 7 containing the first fine emulsion is used together with the present apparatus. It stores a fine emulsion having a particle size of 0.5 µm or less prepared in advance by applying a predetermined pressure to the first mixture of the first hydrophobic compound, emulsifying agent, and aqueous phase. The vessel 7 has a rubber stopper, which is not illustrated, so that the second hydrophobic compound retained in the reservoir unit 10 can be injected into the vessel via the feed pipe 6 while keeping the hermetically sealed condition.

A preparation process of the agent by using the present apparatus will next be described. The reservoir unit 10 of the preparation apparatus illustrated in FIG. 5 stores therein the second hydrophobic compound. It is possible to place a plurality of reservoirs containing hydrophobic compounds different in kind, respectively. A predetermined amount of the second hydrophobic compound is taken out from the reservoir unit via the feed pipe 6 and injected into the vessel containing the first fine emulsion, which vessel is fixed to the fixing unit 8. At the stirring unit, the first emulsion and the second hydrophobic compound in the vessel whose hermetically sealed condition has been maintained are stirred at a rate of approximately 3,000 rpm or greater until they become an apparently single phase, without causing phase separation, to embed the second hydrophobic compound in the first fine emulsion, whereby a second fine emulsion having a particle size of 0.5 µm or less can be prepared. In accordance with the above-described process by using the apparatus having the structure as shown in the present example and therefore having high portability, diagnostic or therapeutic agents having a micron size or less as shown in Examples 1 to 5 can be prepared.

The present invention makes it possible to prepare a phase shift contrast agent just before use while controlling their properties such as in-vivo residence time and ultrasonic sensitivity. The present invention is therefore useful in the drug manufacture, diagnosis, and medical fields.

What is claimed is:

1. A method of preparing an emulsion containing hydrocarbons, comprising:
    preparing a first fine emulsion having a particle diameter of 0.5 µm or less by applying a pressure to a first mixture comprising a first compound which contains at least one compound selected from the group consisting of linear hydrocarbons, branched hydrocarbons, linear fluorinated hydrocarbons, and branched fluorinated hydrocarbons, an emulsifying agent, and an aqueous phase;
    storing the prepared first fine emulsion in a vessel in a hermetically sealed state;
    adding a second compound which contains at least one compound selected from the group consisting of linear hydrocarbons, branched hydrocarbons, linear fluorinated hydrocarbons, and branched fluorinated hydrocarbons, to the prepared first fine emulsion stored in the vessel in the hermetically sealed state, thereby preparing a second mixture; and
    stirring, in the vessel, the second mixture in the hermetically sealed state to embed the second compound in the first fine emulsion, thereby obtaining a second fine emulsion, which contains both the first compound and the second compound, having a particle diameter of 0.5 µm or less,
    wherein the second compound has a boiling point which is less than a boiling point of the first compound.

2. The method according to claim 1, wherein the first compound and the second compound are structural analogs.

3. The method according to claim 1, wherein the first compound has a boiling point of 37° C. or greater and the second compound has a boiling point less than 37° C.

4. The method according to claim 1, wherein the first compound contains at least one compound selected from the group consisting of perfluorohexane, perfluoroheptane, perfluorooctane, and hexane.

5. The method according to claim 1, wherein the second compound contains at least one compound selected from the group consisting of perfluoro-n-pentane and isopentane.

6. The method according to claim 1, wherein the emulsifying agent contains at least one compound selected from the group consisting of phospholipids, vitamin E derivatives, amphiphatic proteins, albumin, and polymers containing polyethylene glycol.

7. The method according to claim 1, wherein the stirring step is performed while controlling the temperature at 0° C. or greater but not greater than 10° C.

8. The method according to claim 1, wherein the first fine emulsion is prepared by a step of applying a pressure of 1 MPa or greater but not greater than 40 MPa.

9. The method according to claim 1, further comprising:
    filtering the second fine emulsion to remove foreign matter.

10. A method of preparing an emulsion containing perfluorocarbons, comprising:
    preparing a first fine emulsion having a particle diameter of 0.5 µm or less by applying a pressure to a first mixture comprising a perfluoroheptane, an emulsifying agent, and an aqueous phase;
    storing the prepared first fine emulsion in a vessel in a hermetically sealed state;
    adding a perfluoro-n-pentane to the prepared first fine emulsion stored in the vessel in the hermetically sealed state, thereby preparing a second mixture; and
    stirring, in the vessel, the second mixture in the hermetically sealed state to embed the perfluoro-n-pentane in the first fine emulsion, thereby obtaining a second fine emulsion, which contains both the perfluoroheptane and the perfluoro-n-pentane, having a particle diameter of 0.5 µm or less,
    wherein the perfluoro-n-pentane has a boiling point which is less than a boiling point of the perfluoroheptane.

11. The method according to claim 10, wherein the first mixture includes from 1 to 5% (v/v) of the perfluoroheptane.

12. The method according to claim 10, wherein the second mixture includes from 1 to 5% (v/v) of the perfluro-n-pentane.

13. The method according to claim 10, further comprising:
    filtering the second fine emulsion to remove foreign matter.

* * * * *